(12) United States Patent
Schramm et al.

(10) Patent No.: US 7,315,361 B2
(45) Date of Patent: Jan. 1, 2008

(54) SYSTEM AND METHOD FOR INSPECTING WAFERS IN A LASER MARKING SYSTEM

(75) Inventors: Rainer Schramm, Everett, MA (US); Jonathan Ehrmann, Sudbury, MA (US)

(73) Assignee: GSI Group Corporation, Billerica, MA (US)

( * ) Notice: Subject to any disclaimer, the term of this patent is extended or adjusted under 35 U.S.C. 154(b) by 211 days.

(21) Appl. No.: 11/118,192

(22) Filed: Apr. 29, 2005

(65) Prior Publication Data

US 2006/0244955 A1   Nov. 2, 2006

(51) Int. Cl.
G01N 21/00 (2006.01)
(52) U.S. Cl. .................. 356/237.1; 356/237.2
(58) Field of Classification Search ............ None
See application file for complete search history.

(56) References Cited

U.S. PATENT DOCUMENTS

| | | | |
|---|---|---|---|
| 4,028,728 A | | 6/1977 | Sharp |
| 4,654,562 A | | 3/1987 | Berdat |
| 4,706,168 A | | 11/1987 | Weisner |
| 5,166,985 A | * | 11/1992 | Takagi et al. ............... 382/150 |
| 5,245,671 A | * | 9/1993 | Kobayashi et al. ......... 382/150 |
| 5,247,344 A | * | 9/1993 | Doan ......................... 356/394 |
| 5,555,474 A | * | 9/1996 | Ledger ....................... 356/632 |
| 5,828,449 A | | 10/1998 | King et al. |
| 5,995,218 A | | 11/1999 | Ide |
| 6,118,540 A | | 9/2000 | Roy et al. |
| 6,238,060 B1 | | 5/2001 | Bourn et al. |
| 6,261,919 B1 | | 7/2001 | Omizo |
| 6,509,965 B2 | * | 1/2003 | Fossey et al. ............ 356/237.2 |
| 6,608,676 B1 | | 8/2003 | Zhao et al. |
| 6,630,996 B2 | * | 10/2003 | Rao et al. ................ 356/237.5 |
| 6,633,338 B1 | | 10/2003 | Pelsue et al. |
| 6,947,151 B2 | * | 9/2005 | Fujii et al. .................. 356/612 |
| 6,987,561 B2 | * | 1/2006 | Reznichenko et al. ... 356/237.2 |
| 7,110,106 B2 | * | 9/2006 | Xu et al. ................. 356/237.5 |
| 2002/0186368 A1 | | 12/2002 | Rosengaus et al. |
| 2004/0031779 A1 | | 2/2004 | Cahill et al. |
| 2004/0060910 A1 | | 4/2004 | Schramm |
| 2004/0101000 A1 | * | 5/2004 | Han et al. ...................... 372/22 |
| 2004/0144760 A1 | | 7/2004 | Cahill et al. |

(Continued)

FOREIGN PATENT DOCUMENTS

EP   0685732   8/1999

(Continued)

OTHER PUBLICATIONS

C. VanDommelen, "Choose the Right Lighting for Inspection," Test & Measurement World, Oct. 1, 1996, www.tmworld.com, accessed Jul. 20, 2005.

(Continued)

*Primary Examiner*—Ha Tran Nguyen
*Assistant Examiner*—Richard Isla-Rodas
(74) *Attorney, Agent, or Firm*—Gauthier & Connors LLP

(57) ABSTRACT

An illumination system is disclosed for use in a semiconductor wafer back side inspection assembly. The illumination system includes an illumination source that is configured to direct illumination toward a highly reflective and directionally reflective surface at an angle α of about 45 degrees to about 75 degrees with respect to the surface.

20 Claims, 7 Drawing Sheets

U.S. PATENT DOCUMENTS

2004/0174518 A1 9/2004 Naiki et al.
2005/0001900 A1 1/2005 Kreh et al.
2005/0002023 A1* 1/2005 Kreh et al. .............. 356/237.5

FOREIGN PATENT DOCUMENTS

EP 1424551 6/2004

OTHER PUBLICATIONS

"Basic Scientific Photography: For the Hobbyist, Naturalist, and Student," Kodak Publication No. N-9, Eastman Kodak Company, Rochester, NY, p. 37-38.

B.G. Batchelor et al., "Automated Visual Inspection," IFS (Publications) Ltd, UK, 1985, p. 105.

* cited by examiner

SYSTEM AND METHOD FOR INSPECTING WAFERS IN A LASER MARKING SYSTEM

BACKGROUND

The invention generally relates to semiconductor substrate processing systems and relates in particular to laser marking systems for semiconductor wafers.

Laser marking systems for semiconductor wafers may be employed, for example, in semiconductor wafer processing systems that provide for the relative positioning and control of one or more semiconductor wafers in at least an x direction and a y direction such that laser marking is typically performed in the x y plane, the laser impinging the wafer generally along a z direction. The laser marking system may remain stationary, therefore, while a wafer stage is moved in the x and y directions. The wafer may be about 200 mm to 300 mm in diameter.

As shown in FIGS. 1A and 1B, a semiconductor wafer 10 may include a front side 12 on which a plurality of circuits 14a, 14b, 14c and 14d may be formed. The wafer 10 may later be diced into a plurality of individual circuits 14 following fabrication of the circuit elements 16 and 18 on each circuit 14a-14d. Four such circuits are shown in FIG. 1B. The semiconductor wafer 10 may also include a notch 22 to facilitate the identification of the proper orientation of the wafer 10 within the processing equipment.

In certain applications, it is desirable to also add an identification marking on either the front side or a back side of each circuit. Such marking is typically performed using a laser, and this laser marking may be used to identify not only the circuit but also manufacturing information in connection with each circuit, orientation information regarding the circuit, or performance data regarding the circuit.

In applications in which the front side 12 of the semiconductor wafer 10 includes circuits 14 that are very dense with elements and conductor paths, it is sometimes desirable to provide identification markings on the back side of the semiconductor wafer. For example, FIG. 2A shows the back side 16 of the semiconductor wafer 10, and FIG. 2B shows markings 24 on the back side of each circuit 14a-14d. The marking information may include a wide variety of text or other symbolic information, and is represented in FIG. 2B as a square 20 in the lower right corner of the front side of each circuit 14. Such a markings may be easily machine readable depending on the level of contrast of the marked versus un-marked regions.

The back side of most conventional semiconductor wafers, however, is typically ground to reduce the thickness of the semiconductor wafer so that thinner circuits 14 may be provided. Such grinding to reduce the thickness of the wafer is typically performed in a circular motion, and this causes a large number of very fine grooves 28, for example, in the general shape of a pinwheel to be formed on the surface of the back side 26 of the semiconductor wafer 10. This further complicates the automated detection of any indicia. In particular, incident light on the wafer in parallel with the grind pattern is generally reflected in a more specular manner than light incident on the wafer perpendicular to the grind pattern, which is generally reflected with stronger scattering. The orientation of the grinding grain varies radially and tangentially such that the grind marks appear as large spiral curvilinear patterns 28 across the wafer as shown in FIG. 2A and the grain orientation at each circuit 14a-d may vary as shown in FIG. 2B. The varying orientation and the characteristic pinwheel shape of these patterns are readily apparent by inspecting surface reflections in room lighting conditions. Grind patterns may vary from manufacturer to manufacturer, from lot to lot and from piece to piece. Other patterns with a varying grain direction may result from different grinding processes. The structure of the resulting grooves may be asymmetrical from side to side so that the scattering is asymmetrical from side to side.

One method of laser marking of the wafer 10 is to form a pattern (e.g., 30) into the surface of the back side 26 as shown in FIG. 3A. The depth of a pattern however, (as shown at d in FIG. 3A) may be so large, for example 10 mircons or more, that cracking of the semiconductor wafer may result from such high contrast laser marking. Patterns that avoid cracking may be less than about 10 microns deep for example in the range of 3 to 5 microns or less.

Another method of laser marking of the back side of a semiconductor wafer involves using a laser to provide a molten trace 32 on the back side surface 26, to thereby remove the relief surface provided by the grooves 28, as shown for example in FIG. 3B. Such a trace mark may have a very small depth of relief, of for example, 0 to 1.0 microns, and preferably about 0.5 microns. For example, U.S. Pat. No. 6,261,919, the disclosure of which is hereby incorporated by reference, discloses a system and method for forming a molten trace on the back side of a semiconductor wafer for purposes of marking. See also U.S. Published Patent Applications Nos. 2004/00600910, 2004/0031779 and 2004/0144760, the disclosures of which are hereby incorporated by reference, which each disclose high speed, laser-based marking systems and methods for Chip Scale Packages (CSP) for producing machine readable marks on workpieces and semiconductor devices with reduced sub-surface damage produced thereby.

Such trace marks, therefore, may be made by changing the surface properties of the material, such as a ground silicon substrate, to form indicia. Marks formed may change absorption characteristics and reduce directional scattering effects by changing the surface texture, especially by flattening out the grind pattern. This reduced scattering effect may increase the fraction of specular reflections from the flattened area of the mark. At the same time increased absorption resulting from laser irradiation may reduce total reflections from the marked area. When fine indicia is formed, the feature sizes of the indicia may be similar to the scale of the features of the grinding marks. At the minimum laser marking power, the laser mark will start to appear as the grind mark begins to flatten. At higher powers, features of the grind mark will be further reduced and flattening will increase. At yet higher powers, material may be moved or removed increasing mark depth and spot to spot overlap marks may begin to form. Generally, incomplete flattening is an indication of a substantially minimum mark depth and spot overlap marks indicate a mark depth greater than the minimum.

The indicia laser marked by such marking may be any type of graphical mark, but are typically alphanumeric characters, pin indicators such as filled circles, circuit feature indication marks and chip orientation marks such as chevrons. Smaller die such as, for example, 0.1 by 0.2 mm die may be marked with a dot or orientation mark, while larger die, for example 2.5 mm by 20 mm may be marked with alpha numeric characters.

For CSP marking, the wafer is held in a wafer chuck that allows laser marking of indicia on the backside of die sites across the wafer. High accuracy marking is achieved by marking indicia in a scan field smaller than the size of the wafer, for example, over an 80 mm square field. To cover all of the sites to be marked with indicia on the back of the wafer, the wafer is stepped with a stage relative to marking field.

Although laser marking by altering portions of the relief surface provided by the grooves 28 generally imparts less stress on the wafer, the marks formed thereby are typically more difficult for a detection system to read. The typically very highly reflective nature of the back side of the wafer may make it further difficult for a detection system to read the laser markings for confirmation purposes. Further, the grooves on certain portions of the wafer may be nearly parallel with one another, providing highly directional reflections (such as grooves 28 resulting in pin-wheel type reflection images that rotate with angle of viewing). For this reason, such detection of markings on the back side is generally performed at very close range after each circuit has been diced from the wafer.

In certain applications, however, it would be desirable for a laser marking and wafer processing system to be able to perform inspection of laser markings on the back side of a wafer while the system is also inspecting the top side of the wafer. Correlating such top and bottom inspections provides highly accurate testing of the position of each marking on each circuit prior to dicing. Performing such a correlation requires a back side detection system that can read the back side of a wafer while it is being handled, as well as a front side detection system of the front side of a wafer. Reliable detection of the back side of a wafer, however, has proven to be extremely difficult due to the highly reflective and directionally reflective nature of the back side of the wafer due to the grinding process. Lighting from directly below the back side surface will be brightly reflected resulting in poor image contrast, and lighting from the side along the wafer may cast distractive unwanted highlights and shadows on the back side surface. Illuminating the highly reflective and directionally reflective back side surface for imaging from a distance, therefore, has not been satisfactory. Additionally, the interaction of the illumination with the varying backside grind pattern may create varying image quality across the wafer, and in some areas, image quality may be insufficient for successful image processing.

Further, in many wafer inspection applications, there are required working distance constraints. Wafers in CSP marking systems are typically held around the perimeter or by other areas on the back side of the wafer. Inspecting indicia at the edge of the wafer or at areas near chuck contact requires sufficient working distance from the illuminator and camera to the wafer to avoid mechanical interference or optical disruptions. Optical disruptions may include blocking portions of the illuminating field, light scattering off the chuck or associated mounting structures and onto the wafer, and blocking portions of the camera image field. Available space may be further limited by camera package size and by the imaging lens size.

In certain applications, it is desirable to inspect laser marked indicia on the ground back side of a wafer that is held in a chuck. Available illuminators designed for conventional wafer inspection do not provide images at sufficient working distance and with a uniform image quality for highly reliable inspection of wafer areas when different areas of the wafer are positioned for imaging relative to an inspection camera and illuminator.

There is a need, therefore, for a laser marking and processing system that may provide laser marking on the back side of a wafer, and that may provide automated correlation of the front and back sides of the wafer.

There is further a need for an improved wafer illumination system for inspecting laser marked indicia on the ground back side of a wafer when held in a back side marking chuck

SUMMARY

The invention provides an illumination system for use in a semiconductor wafer back side inspection assembly in accordance with an embodiment. The illumination system includes an illumination source that is configured to direct illumination toward a highly reflective and directionally reflective surface at an angle $\alpha$ of about 45 degrees to about 75 degrees with respect to the surface.

In accordance with another embodiment, the invention provides a semiconductor wafer inspection system that includes a semiconductor wafer handling system, an illumination system, and an inspection system. The semiconductor wafer handling system is for controlling movement of a semiconductor wafer in at least an x direction and a y direction. The illumination system includes an illumination source that is configured to direct illumination toward a highly reflective and directionally reflective surface of the semiconductor wafer at an angle $\alpha$ of about 45 degrees to about 75 degrees with respect to the highly reflective and directionally reflective surface of the semiconductor wafer. The inspection system includes a camera that is directed toward the highly reflective and directionally reflective surface of the semiconductor wafer from a distance of at least about 100 mm.

In accordance with a further embodiment, the invention provides a semiconductor wafer inspection system that includes a semiconductor wafer handling system, an illumination system, an inspection system and a controller. The semiconductor wafer handling system is for controlling movement of a semiconductor wafer in at least an x direction and a y direction. The illumination system includes an illumination source that is configured to direct high frequency illumination toward a highly reflective and directionally reflective surface of the semiconductor wafer at an angle $\alpha$ of about 50 degrees to about 70 degrees with respect to the highly reflective and directionally reflective surface of the back side of the semiconductor wafer. The inspection system includes a camera that is directed toward the highly reflective and directionally reflective surface of the semiconductor wafer from along a z direction a distance of about 115 mm. The controller is for processing image data that is provided by said camera and for performing other system functions.

BRIEF DESCRIPTION OF THE ILLUSTRATED EMBODIMENTS

The following detailed description may be further understood with reference to the accompanying drawings in which.

The drawings are shown for illustrative purposes only and are not to scale.

DETAILED DESCRIPTION OF THE ILLUSTRATED EMBODIMENTS

The invention provides an illumination system in a wafer inspection assembly. In accordance with an embodiment, the invention provides illumination for high contrast imaging of laser marked grainy specular target areas having variable grain orientation on the back side of ground silicon wafers. Such an illumination system permits laser marked indicia on the back side of the ground wafers to be reliable inspected while the wafers are being processed in the inspection assembly. The features of the laser marked indicia may be differentiated from the wafer grind marks due, in part, to the illumination provided by the illumination system.

Figure 1A:
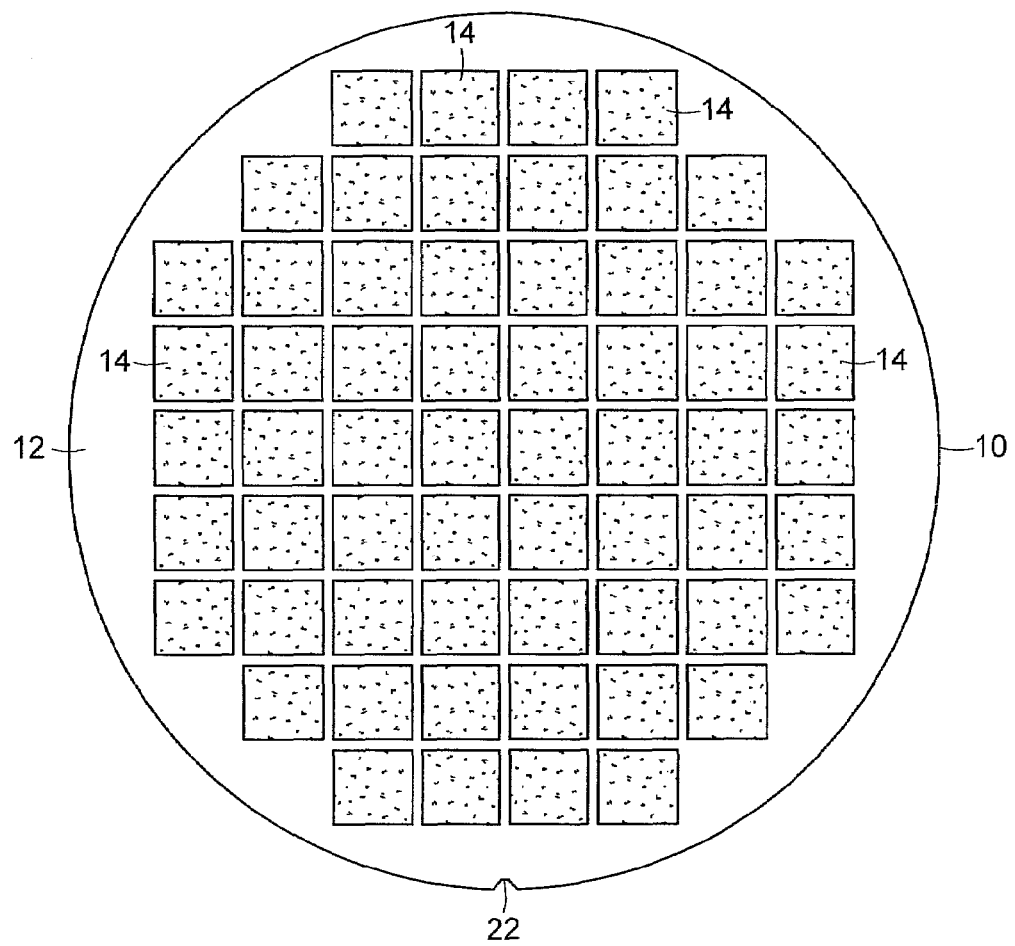
FIG. 1A shows an illustrative diagrammatic view of a front side of a semiconductor wafer on which a plurality of circuits may be formed in accordance with the prior art.
Figure 1B:
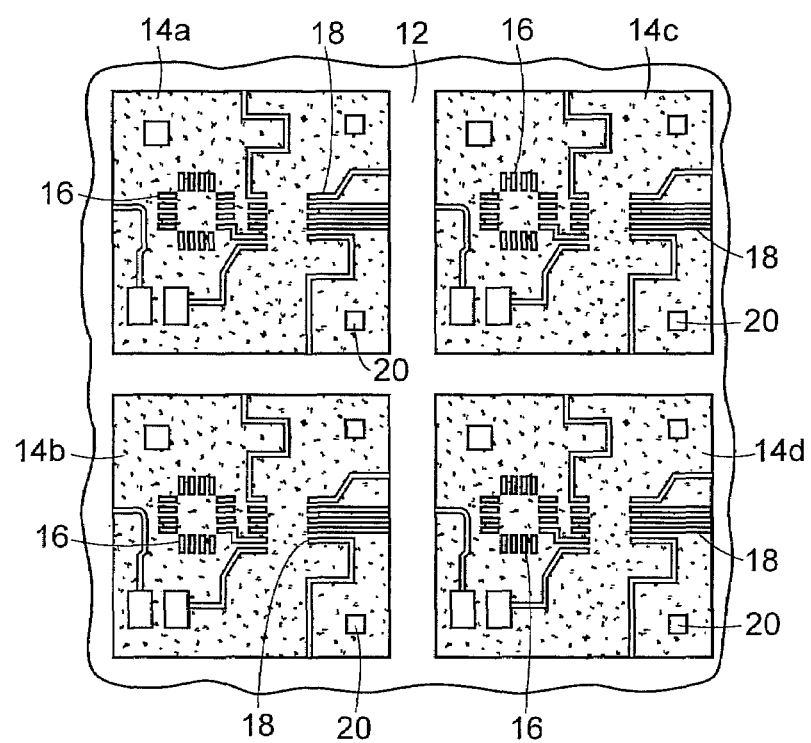
FIG. 1B shows an illustrative diagrammatic view of a portion of the view shown in FIG. 1A including a subset of the plurality of circuits.
Figure 2A:
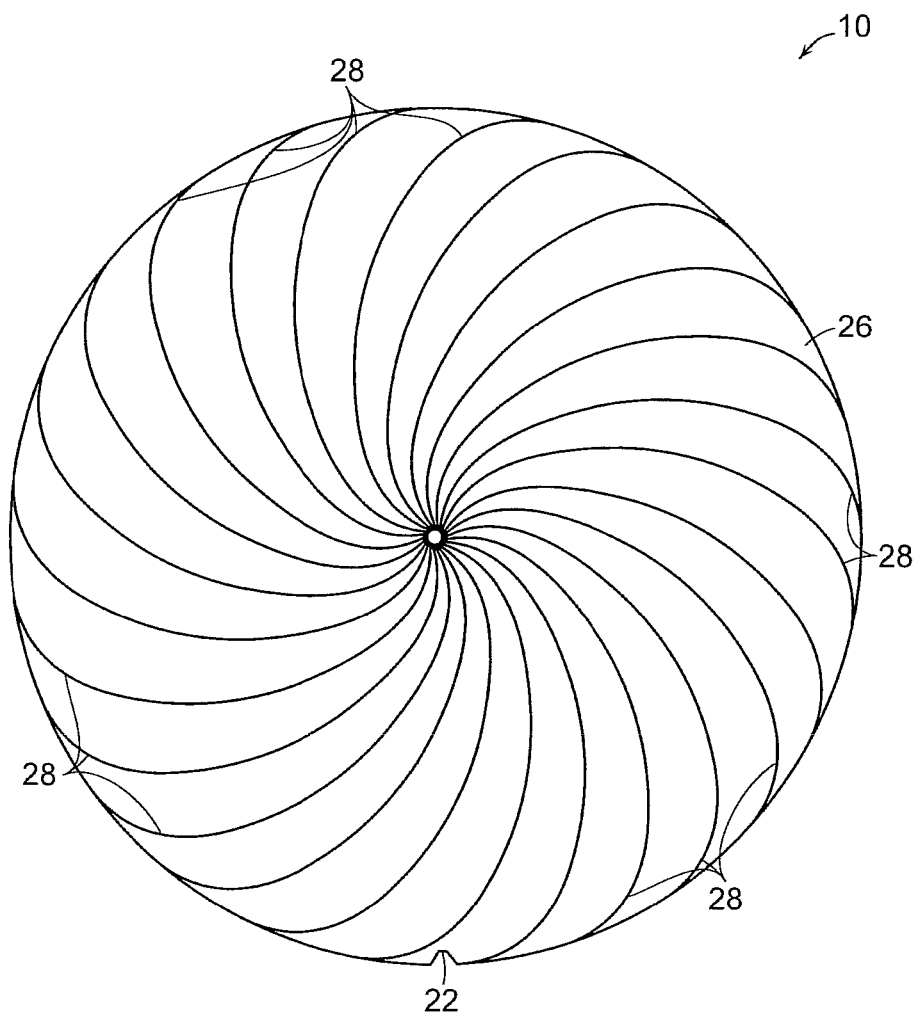
FIG. 2A shows an illustrative diagrammatic view of a back side of a semiconductor wafer on which a plurality of circuits may be formed in accordance with the prior art.
Figure 2B:
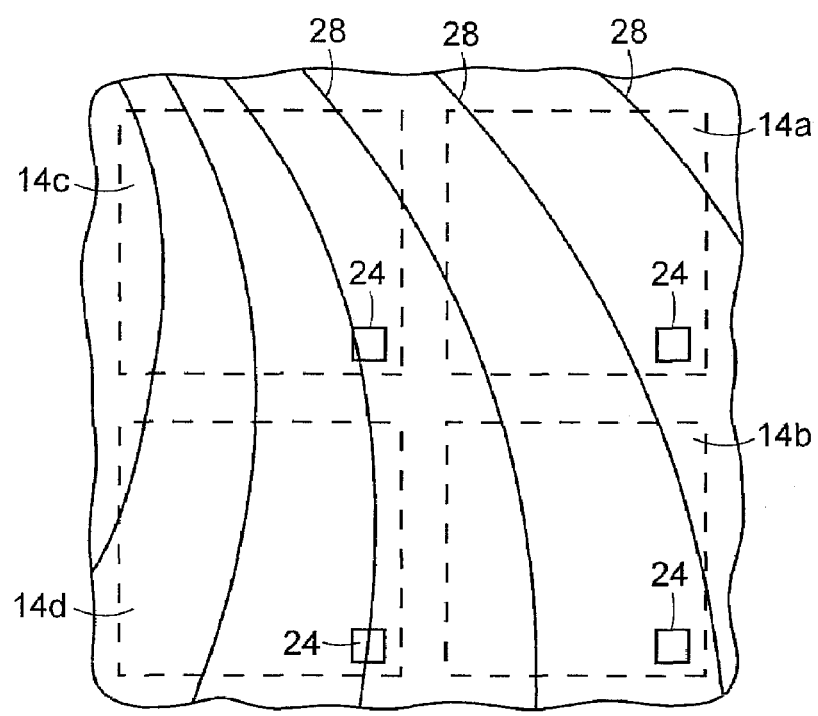
FIG. 2B shows an illustrative diagrammatic view of a portion of the view shown in FIG. 2A including a marking on the back side of a subset of the plurality of circuits.
Figure 3A:
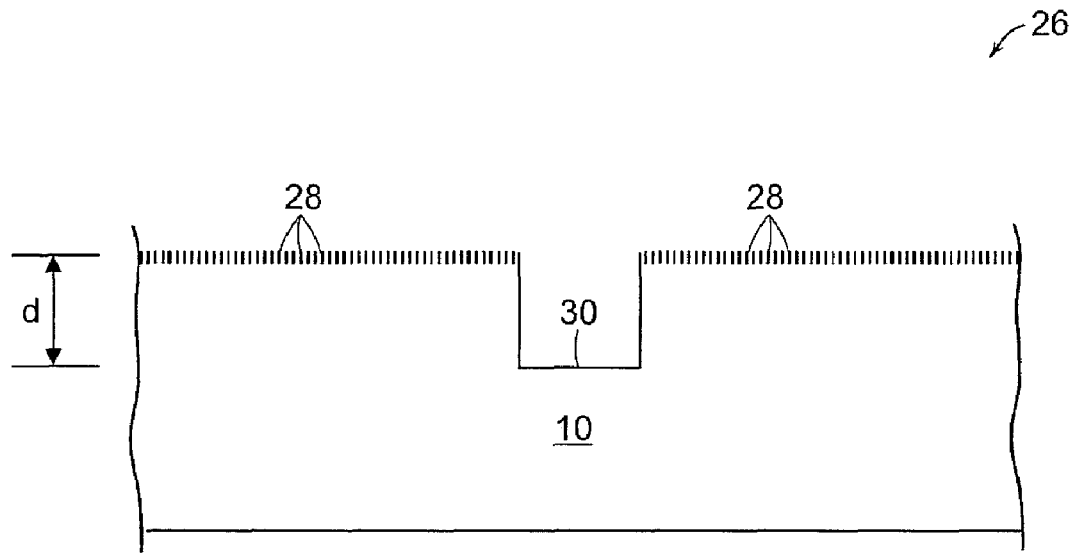
FIG. 3A shows an illustrative diagrammatic side sectional view of a portion of a semiconductor wafer including indicia on the back side thereof (shown facing up) in accordance with a marking technique of the prior art.
Figure 3B:
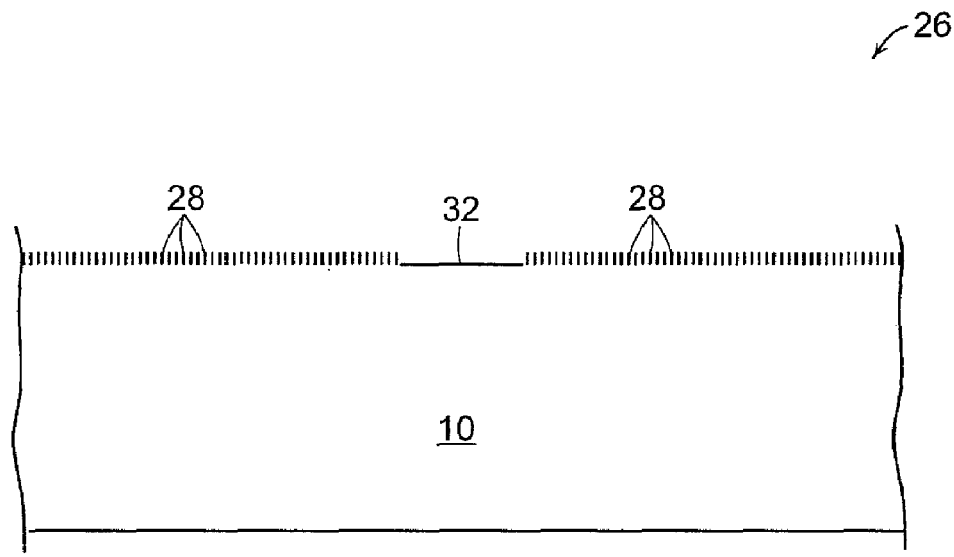
FIG. 3B shows an illustrative diagrammatic side sectional view of a portion of a semiconductor wafer including indicia on the back side thereof (shown facing up) in accordance with another marking technique of the prior art.
Figure 4:
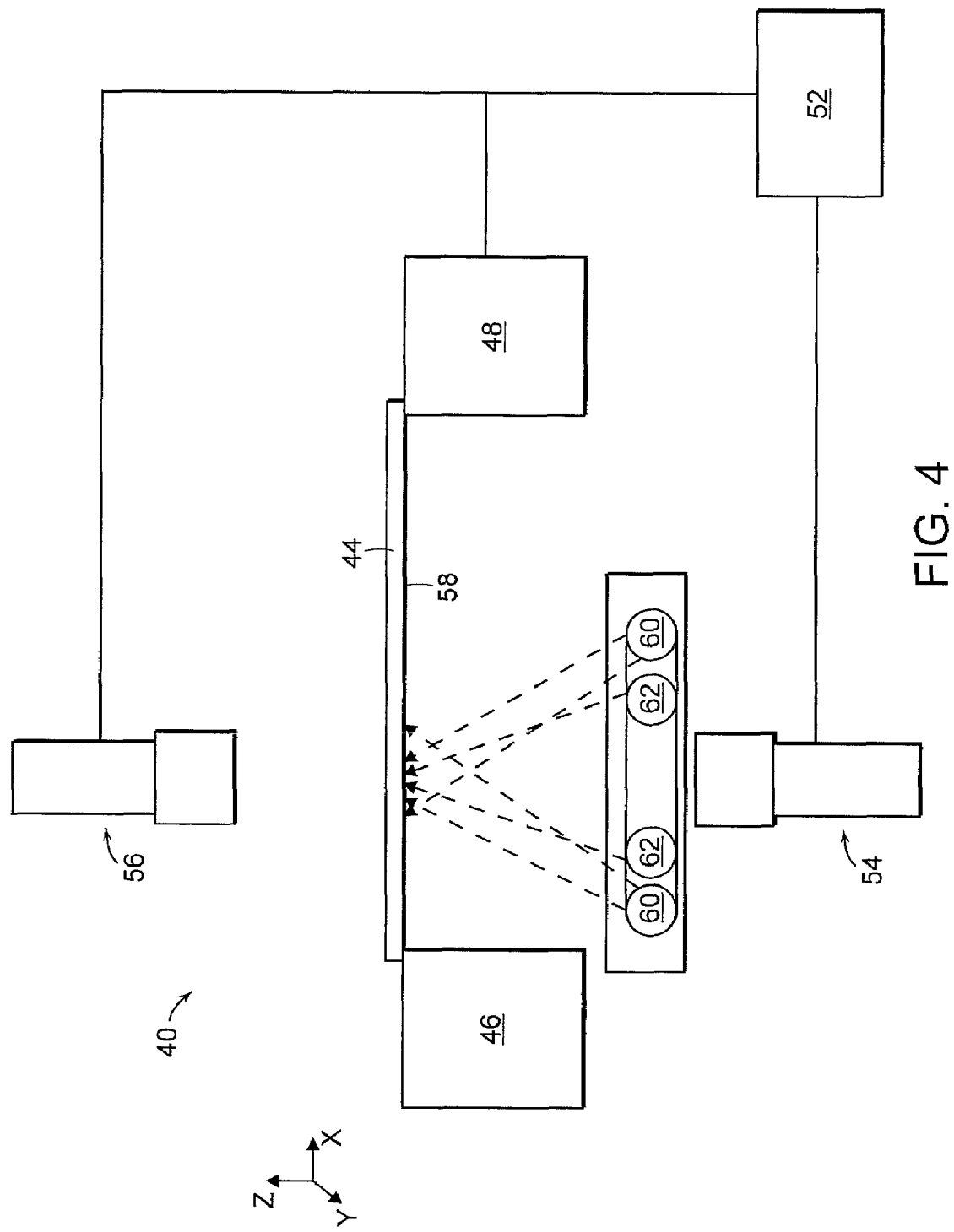
FIG. 4 shows an illustrative diagrammatic view of a wafer marking and imaging system in accordance with an embodiment of the present invention.
Figure 5:
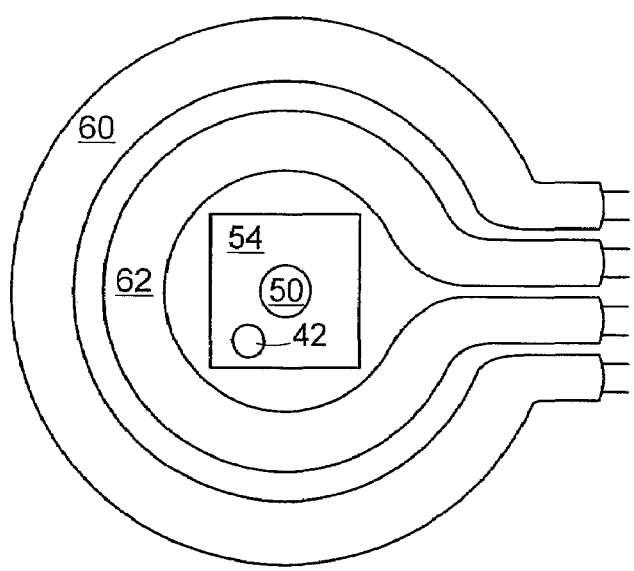
FIG. 5 shows an illustrative diagrammatic top view of the lighting system shown in FIG. 4.
Figure 6:
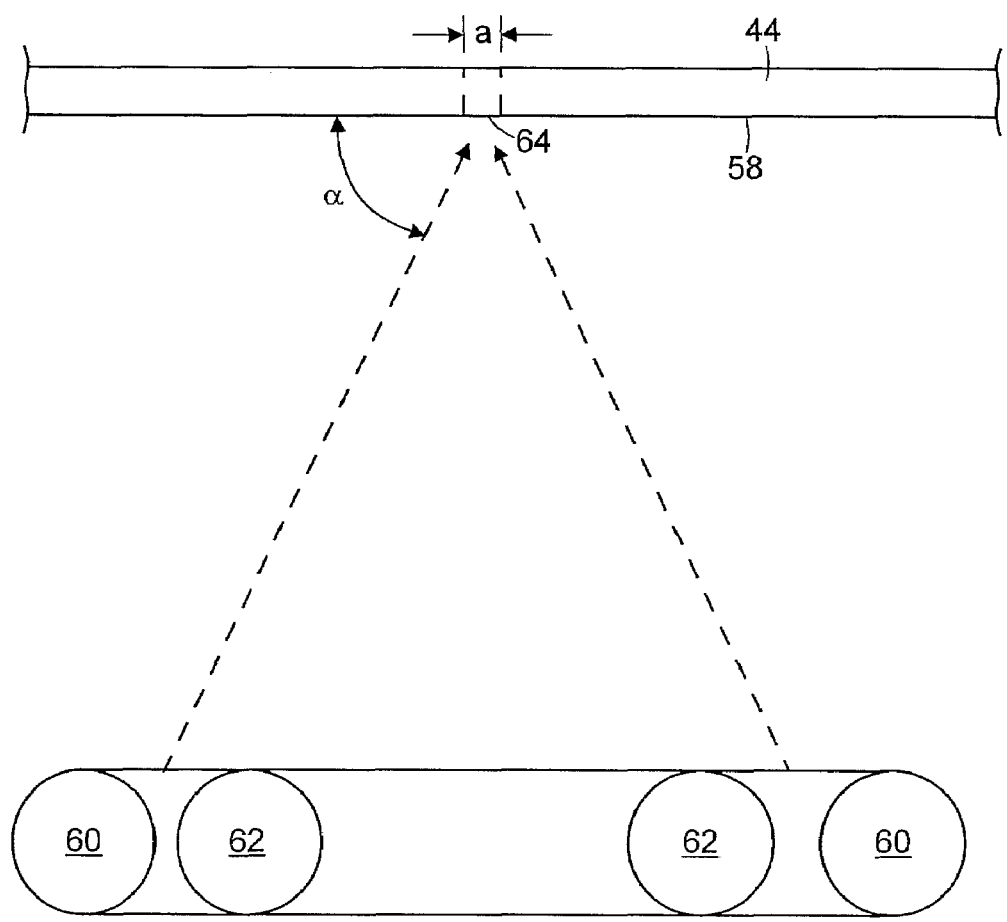
FIG. 6 shows an illustrative diagrammatic enlarged side view of a portion of the system shown in FIG. 5.

As shown in FIGS. 4-6, a laser processing system 40 in accordance with an embodiment of the invention includes a laser marking system 42 (shown in FIG. 5) for forming indicia on a substrate 44, a positioning system including chucks 46 and 48 for positioning the substrate 44 relative to the marker 42, a back side inspection system 50 for detecting the indicia, and a system controller 52 for coordinating operation of the marking system 42, positioning system, and inspection system 50. The marking system 42 and the inspection system 50 may be provided in a unitary housing 54. The system may also include a front side inspection system 56 that is also coupled to the controller 52.

The illumination system for the back side inspection system 50 includes a pair of concentric fluorescent ring lights 60 and 62 with a central aperture that permit the back side inspection system 50 to be directed toward the back side 58 of the substrate 44 through the central aperture of the ring lights 60 and 62 as shown. The illumination from the ring lights generally approaches the target area 64 having a width w on the back side 58 of the substrate 44 from an average angle of about α as shown in FIG. 6. The ring lights may be high frequency (e.g., about 25 kHz) fluorescent ring lights. The angle α may be about 45 to about 75 degrees, and is preferably about 50 to about 70 degrees.

In accordance with an embodiment, therefore, the invention provides an inspection system for detecting indicia formed on a semiconductor wafer surface that includes indicia to be detected, and also that includes surface marks proximate to or intersecting the indicia. The system includes an imager having a field of view along a z axis for imaging the surface, and for detecting indicia 64 within an image of the surface 58. In various embodiments, the system includes an illuminator having at least one source for emitting radiant energy that impinges the surface from a mid range angles and produces reflected radiant energy from the surface that is imaged with the imaging sub-system. The source is disposed such that the energy is emitted at a sufficient distant from the surface to substantially avoid physical interference and is emitted encircling the field of view axis within in a range of incident angles such that variation within the image caused by the surface marks is reduced while avoiding imaging strong reflections from the surface marks. The indicia may thereby be discriminated from the surface marking within at least a pre-determined portion of a field of view of the imager.

In accordance with various embodiments, the surface marks may be curvilinear. The strong reflections may be at least partially specular reflections. The surface reflection may be sensitive to incident angle and orientation. The surface marks may be marks that are formed with a tool during a processing step prior to forming indicia with the laser marker at the marking station. The surface may be a back side of a silicon substrate. The source may emit the radiant energy in substantially all directions and may be annular and/or toroidal, and may include a diffuse reflector. The source may provide high frequency emission and may be a white light or colored light source. In source may also include a plurality of diffuse sources, and the emission of the radiant energy may occur in a plane that is substantially parallel to the surface.

The distance between the source and the back side surface to be imaged may be at least 100 mm (e.g., about 110 m-130 mm) and the field of view range of the detection system (FOV) may be in the range of about 6 mm to 15 mm. The indicia formed with the laser marker may have a depth of 1 micron or less. In an embodiment the inspecting indicia are marked with sufficient energy to reduce residual intersecting grind marks and low enough energy to avoid the formation of overlap marks thereby increasing template matching thresholds. The template matching thresholds may be 10% or higher, and in a certain embodiments may be 30% or higher.

It has been found that bright field illumination of CSP indicia, when light from the reflective indicia is received by the camera, yields relatively poor contrast due to the highly specular reflecting content of both the indicia and the adjacent unmarked substrate. It has also been found that dark field illumination can provide higher image contrast and therefore it is preferred for imaging indicia on CSP. In this dark field imaging technique, the unmarked background scatters light that is received by the camera and the laser marked indicia reflect and absorb light that is not received by the camera. Diffuse sources are preferred to reduce contrast in the grind mark texture.

The source angle is preferably small enough to avoid strong specular reflections, and the illumination source is preferably omni-directional (e.g., a ring source) to further reduce variation of image quality with wafer position. Omni-directional illumination may also reduce the contrast of grind mark texture. Higher output sources are preferred, and multiple sources and efficient diffusers such as light shaping diffusers may be used to provide sufficient illumination levels.

In an example of a system of an embodiment of the invention, the laser marking may be achieved with a commercially available CSP marking system using a green frequency doubled Nd:YVO4 laser, for example the GSI Lumonics model CSP200 as sold by GSI Lumonics Corporation of Wilmington, Mass. Marking parameters will vary with different wafer types and grind patterns but typical laser parameters for trace marks (also called black marks) of <1 μm in depth may be as follows: Q-Switch Frequency:

30000-33000 Hz; Scan Speed: 200-500 mm/sec; Power: 2.5-3.5 W; Q-switch Pulse width: 10-13 μsec; Spot Size: 40-60 μm; Scan lens: f=200 mm; Scan field: 80 mm*80 mm; and Pulse Width: 15 ns. Laser marking may be achieved in the following general ranges: Q-Switch Frequency: 20000-40000 Hz; Scan Speed: <1200 mm/sec; Power: 1.8-5 W; and Spot Size: <72 μm.

In the CSP200 system, the wafer is moved with a precision x-y table that carries the wafer chuck, but other types of relative motion systems could be used. The working distance is approximately 165 mm from the wafer to the imaging lens. The camera is a $V_2$ CMOS mega pixel type (e.g., a CDC-100 sold by Cognex Corporation of Needham, Mass.), but other types such as CCD sensors, and other imager size formats are possible. The imaging lens provides a 55 mm telecentric type focal length and the imaged field size is 12 mm×8 mm with about 3 pixels per 50 micron mark feature. The telecentric lens is preferred for reduced variation in the illuminated image contrast with the incident viewing angle, as well as reduced positional errors with target height. Optionally, a 2× lens adaptor may be used to increase resolution to about 6 pixels per 50 microns mark feature, which in some cases is preferred for improved inspection quality. The target area is at least a portion one or more marked die sites within the field of view of the camera, and one or more of the laser marked indicia at one or more die sites is inspected. The image can be processed with a commercially available machine vision system, for example with Cognex PatMax software.

The preferred illumination system includes a StockerYale Super Light model 18 high frequency fluorescent ring lights (sold by StockerYale, Inc. of Salem, N.H.), which has highly diffuse output and can be set up for intermediate illumination angles high enough to reduce grind mark contrast and low enough to avoid strong specular reflections, e.g., preferably about 45 to 55 degrees. Typical working distance for the illuminator is about 115 mm. The model 18 ring light may be used with standard white fluorescent tubes at a color temperature of 5100° K or with other available tubes with alternate color temperatures and discrete colors, for example blue tubes at 450 nm, which may be preferred for certain type of wafers. Other types of illuminators are possible with high output intermediate illumination angles. A diffuse light is preferred, but dense (e.g. LED) arrays with sufficient output may also provide improved imaging.

An illustrative example of improvement is from a level of about 50% of selected sites successfully inspected when clusters of LEDs are used to a level of about 92% of selected sites successfully inspected with the preferred fluorescent ring light at an intermediate illumination angle using a 30% template matching threshold.

Those skilled in the art will appreciate that numerous modifications and variations may be made to the above disclosed embodiment without departing from the spirit and scope of the invention.

What is claimed is:

1. A semiconductor wafer inspection system comprising:
   a semiconductor wafer handling system for controlling movement of a semiconductor wafer in at least an x direction and a y direction;
   an illumination system including a ring light, said illumination system being configured to direct diffuse illumination toward a highly reflective and directionally reflective surface of the semiconductor wafer at an angle α of about 45 degrees to about 75 degrees with respect to the highly reflective and directionally reflective surface of the semiconductor wafer; and
   an inspection system including a camera that is directed toward the highly reflective and directionally reflective surface of the semiconductor wafer from a distance of at least about 100 mm and that is positioned to have an optical path that extends through an opening in the ring light.

2. The semiconductor wafer inspection system as claimed in claim 1 wherein said angle α is between about 50 degrees and about 70 degrees.

3. The semiconductor wafer inspection system as claimed in claim 1 wherein said ring light is positioned a distance of about 100 mm from the highly reflective and directionally reflective surface.

4. The semiconductor wafer inspection system as claimed in claim 1 wherein said ring light is generally provided along a first plane that is substantially parallel with the highly reflective and directionally reflective surface.

5. The semiconductor wafer inspection system as claimed in claim 1 wherein said inspection assembly includes a detection system that detects indicia on the back side of the semiconductor wafer using illumination provided by the ring light.

6. The semiconductor wafer inspection system as claimed in claim 5, wherein said system further includes a front side inspection system that is directed toward a front surface of the semiconductor wafer.

7. The semiconductor wafer inspection system as claimed in claim 5, wherein said system further includes a laser marking system for providing indicia on a semiconductor wafer.

8. The semiconductor wafer inspection system as claimed in claim 1, wherein said system further includes a controller for processing image data that is provided by said camera, and said controller is able to distinguish marking indicia from wafer grind lines when the marking indicia has a depth of less than 1 micron.

9. The semiconductor wafer inspection system as claimed in claim 1, wherein said ring light is a fluorescent ring light.

10. The semiconductor wafer inspection system as claimed in claim 1, wherein said illumination system includes plurality of a fluorescent ring lights.

11. A semiconductor wafer inspection system comprising:
    a semiconductor wafer handling system for controlling movement of a semiconductor wafer in at least an x direction and a y direction;
    an illumination system including at least one fluorescent ring light that is configured to direct high frequency illumination toward a highly reflective and directionally reflective surface of the semiconductor wafer at an angle α of about50 degrees to about70 degrees with respect to the highly reflective and directionally reflective surface of the back side of the semiconductor wafer;
    an inspection system including a camera that is directed toward the highly reflective and directionally reflective surface of the semiconductor wafer from along a z direction at a distance of about 115 mm and that is positioned to have an optical path that extends through an opening in the fluorescent ring light; and
    a controller for processing image data that is provided by said camera.

12. The semiconductor wafer inspection system as claimed in claim 11, wherein said controller distinguishes marking indicia from wafer grind lines when the marking indicia has a depth of less than 1 micron.

13. The semiconductor wafer inspection system as claimed in claim 11, wherein said illumination system includes a plurality of high frequency fluorescent ring lights.

14. The semiconductor wafer inspection system as claimed in claim 11, wherein said highly reflective and directionally reflective surface of the back side of the semiconductor wafer is ground in a spiral pattern.

15. The semiconductor wafer inspection system as claimed in claim 11, wherein said controller for processing said image data applies a template matching threshold of at least 30%.

16. A semiconductor wafer inspection system comprising:
a semiconductor wafer handling system for controlling movement of a semiconductor wafer in at least an x direction and a y direction;
an illumination system including a plurality of high frequency fluorescent ring lights that are configured to direct high frequency illumination toward a highly reflective and directionally reflective surface of the semiconductor wafer at an angle a of about 50 degrees to about 70 degrees with respect to the highly reflective and directionally reflective surface of the back side of the semiconductor wafer;
an inspection system including a camera that is directed toward the highly reflective and directionally reflective surface of the semiconductor wafer from along a z direction at a distance of about 115 mm; and
a controller for processing image data that is provided by said camera.

17. The semiconductor wafer inspection system as claimed in claim 16, wherein said camera is positioned to have an optical path that extends through an opening in the high frequency fluorescent ring lights.

18. The semiconductor wafer inspection system as claimed in claim 16, wherein said controller distinguishes marking indicia from wafer grind lines when the marking indicia has a depth of less than 1 micron.

19. The semiconductor wafer inspection system as claimed in claim 16, wherein said highly reflective and directionally reflective surface of the back side of the semiconductor wafer is ground in a spiral pattern.

20. The semiconductor wafer inspection system as claimed in claim 16, wherein said controller for processing said image data applies a template matching threshold of at least 30%.

\* \* \* \* \*

UNITED STATES PATENT AND TRADEMARK OFFICE
CERTIFICATE OF CORRECTION

PATENT NO. : 7,315,361 B2  Page 1 of 1
APPLICATION NO. : 11/118192
DATED : January 1, 2008
INVENTOR(S) : Schramm et al.

It is certified that error appears in the above-identified patent and that said Letters Patent is hereby corrected as shown below:

In Claim 11, Col. 8, line 52, please delete "about50" and replace with --about 50-- and delete "about70" and replace with --about 70--.

Signed and Sealed this

Twenty-ninth Day of April, 2008

JON W. DUDAS
*Director of the United States Patent and Trademark Office*